United States Patent [19]

Masters et al.

[11] Patent Number: 4,681,567
[45] Date of Patent: Jul. 21, 1987

[54] SYRINGE WITH SAFETY SHEATH

[76] Inventors: Edwin J. Masters, 142 Autumn, Sikeston, Mo. 63801; Paul L. Ebaugh, 1553 Lexington, Cape Girardeau, Mo. 63701

[21] Appl. No.: 847,757

[22] Filed: Apr. 3, 1986

[51] Int. Cl.⁴ ............................................. A61M 5/32
[52] U.S. Cl. .................................................. 604/198
[58] Field of Search ............... 604/198, 197, 192, 263, 604/187

[56] References Cited

U.S. PATENT DOCUMENTS

| | | | |
|---|---|---|---|
| 2,571,653 | 10/1951 | Bastien . | |
| 3,487,834 | 1/1970 | Smith, Jr. et al. | 604/197 X |
| 3,780,734 | 12/1973 | Wulff . | |
| 3,890,971 | 6/1975 | Leeson et al. . | |
| 4,373,526 | 2/1983 | Kling | 604/198 |
| 4,425,120 | 1/1984 | Sampson et al. | 604/198 |
| 4,631,057 | 12/1986 | Mitchell | 604/198 |

*Primary Examiner*—John D. Yasko
*Attorney, Agent, or Firm*—Rogers, Howell, Moore & Haferkamp

[57] ABSTRACT

An improved syringe of the type comprising a barrel having a needle extending from the lower end, the syringe further comprising a knob extending outwardly from the barrel near the lower end, and a sheath slideably mounted on the barrel and slideable between a retracted position and an extended position. The sheath has a slot for receiving the knob, the slot having tabs for releasably retaining the sheath in its retracted position releasable upon downward pressure applied to the sheath, and tabs for lockingly engaging the knob to lock the sheath in the extended position.

22 Claims, 14 Drawing Figures

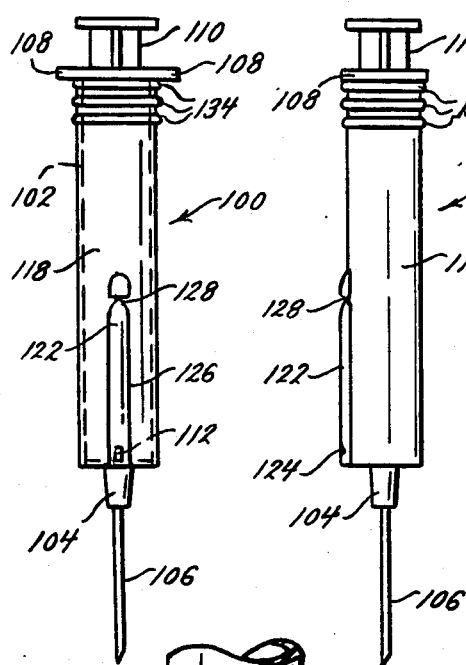
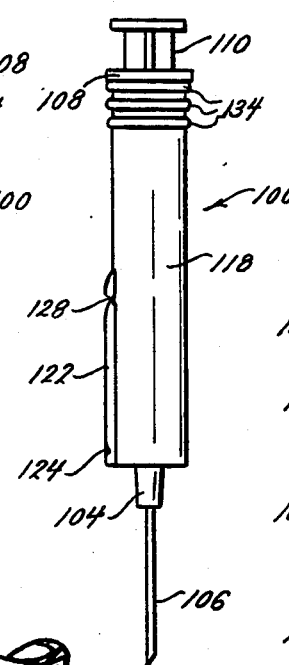
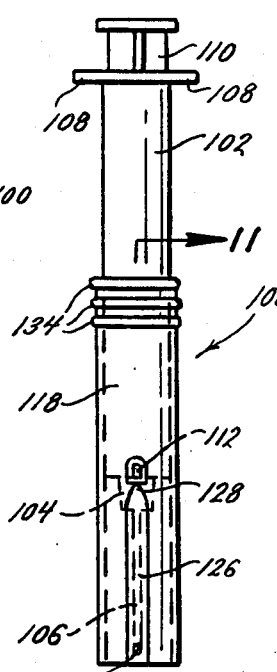
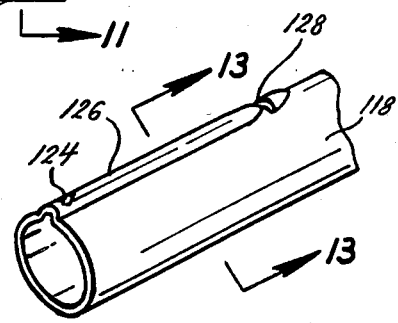
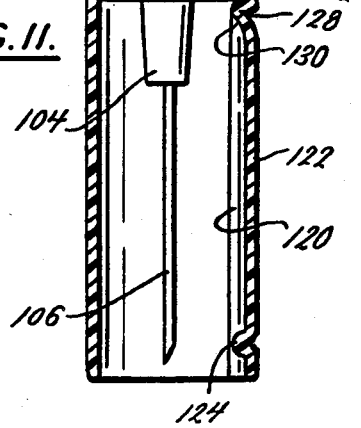

SYRINGE WITH SAFETY SHEATH

BACKGROUND AND SUMMARY OF THE INVENTION

This invention relates to improvements in syringes and in particular to a syringe having a safety sheath for preventing needlesticks.

Hypodermic needles, for example those used for injections or for taking blood samples, are usually equipped with a removeable cap that protects and helps keep the needle sterile. The cap is usually replaceable to cover the used, contaminated needle and prevent accidental needlesticks. However, accidental needlesticks during recapping have long been a problem. Because of tension, time pressure, or fatigue, needlesticks during recapping occur with alarming frequency despite frequent warnings to be careful, and they account for the majority of accidental needlesticks. Eliminating recapping will not solve the problem because the uncapped needle is so dangerous. Indeed, a large number of accidental needlesticks are caused by uncapped needles found in beds, on floors, or in garbage cans. Even where there is a no recapping policy, the needles are often recapped because of these dangers.

Accidental needlesticks are serious because they can spread diseases, including hepatitis, venereal diseases, and of most recent concern: AIDS. A needlestick causes fear and anxiety in the victim. Both the victim and the patient may be subjected to a battery of expensive, time-consuming tests. Accidental needlesticks during recapping can cost even a relatively small health care institution thousands of dollars annually. Even worse than the economic cost, however, is the transmission of disease.

For example, the victim of a needlestick from a needle contaminated by an AIDS patient must be repetitively tested for several months after the accident. It is documented that after such a needlestick, the victim may test positive for exposure to the AIDS virus, even if the disease is not contracted. A positive test would cause great fear and anxiety in the victim, would seriously disrupt the victim's personal life, and might even end the victim's ability to work in health care.

Despite the very serious nature of the problem, and the severity of the consequences, the problem of accidental needlesticks has persisted for many years without any satisfactory solution. One approach to a solution is to modify the cap. For example, a recent article Sumner, "Needlecaps to Prevent Needlestick Injuries", INFECTION CONTROL (1985) Vol. 6, No. 12, p. 495, discusses the needlestick problem and discloses a needlecap with a small, wide angle funnel surrounding the cap opening. This funnel acts as both a guide and a shield. However, improvements to the cap do not totally eliminate the possibility of needlesticks. The action of bringing the cap and needle together still poses the threat of an accidental needlestick.

Another approach to a solution is to provide a sheath that can be slid down over the needle from behind, eliminating the risky action of bringing the cap and needle together. There have been several syringe constructions having sheaths that can be slid down over the needle. Bastien, U.S. Pat. No. 2,571,653 discloses a Syringe having a sheath slideably mounted over the barrel to hide the needle from view. The sheath has a V-shaped latch that can engage grooves in the barrel of the syringe. This is not a safety device, but merely a device to hide the needle from the patient; the sheath is designed to be freely moveable to expose the needle. Wulff, U.S. Pat. No. 3,780,734 discloses a Hypodermic Syringe Holder and Injector Device having a slideably mounted guard. This is not a syringe but a syringe holder, and is designed for veterinary use. The device would be cumbersome to use and difficult and expensive to make. When the used syringe is removed from the device, the needle will be exposed. Leeson et al., U.S. Pat. No. 3,890,971 discloses a Safety Syringe having a lockable plunger and a lockable, slideable needle cap. The device is very complex and would be difficult and expensive to make. Sampson et al., U.S. Pat. No. 4,425,120, discloses a Shielded Hypodermic Syringe having a needle guard mounted on the syringe barrel for movement between an extended position shielding the needle and a retracted position. The guard is lockable in each position with tracks on the inside of the guard and track engaging members on the barrel. This device would be difficult to operate because the tracks must be aligned with the track engaging members, and it requires a twisting motion to lock and unlock the needle guard. The device would also be difficult and expensive to make.

The inventors have developed a syringe with a safety sheath that eliminates the need for recapping the syringe after use. The sheath is slideably mounted over the barrel of the syringe and after use is simply slid downwardly to its extended position over the needle until it locks, thereby shielding the needle. The syringe has at least one knob projecting outwardly from the barrel. The sheath also has at least one longitudinal slot for receiving the knob. The slot has a first set of opposing tabs projecting into the slot, the lower faces of which engage the top of the knob to retain the sheath in its retracted position. The lower faces of the first set of tabs are angled. These angled lower faces force the tabs apart to clear the knob when the sheath is forced downwardly against the knob. The slot also has a second set of opposing tabs projecting into the slot above the first set. The second set of tabs have angled lower faces and flat upper faces that form a shoulder. The angled lower faces force the tabs apart to clear the knob when the sheath is forced downwardly against the knob. The tabs resiliently snap back after clearing the knob, and the shoulders formed by the upper faces of the tabs engage the bottom surface of the knob and lock the sheath in the extended position.

The syringe of the present invention has a safety sheath that is retained in its retracted position until positive force is applied to overcome the resistance of the first set of tabs. The sheath is easily operated to its extended position by simply pushing the sheath downward. The sheath is easily locked in its extended position by simply pushing the sheath all the way down until the second set of tabs engage the knob. This positive locking action requires no special alignment or manipulation. The locking is positive and easy to visually confirm.

The syringe of the present invention is of simple construction and will be easy and inexpensive to make and simple to use. The locking action is positive and visually confirmable, and without any special manipulation that can be improperly done. The syringe can thus be widely used to eliminate the dangers of needlesticks during recapping.

BRIEF DESCRIPTION OF THE DRAWINGS

FIG. 8 is a side elevation view of a second embodiment of a syringe with a safety sheath constructed according to the principles of this invention, with the safety sheath in the retracted position;

FIG. 9 is a second side elevation view of the syringe turned to show the tunnel in the safety sheath for receiving the knob on the syringe barrel;

FIG. 10 is a side elevation view of the syringe with the safety sheath in the extended position;

FIG. 11 is a partial cross-sectional view of the syringe taken along the plane of line 11—11 in FIG. 10, showing the engagement between the knob and the safety sheath in the extended position;

FIG. 12 is a partial perspective view of the lower end of the safety sheath;

FIG. 13 is a cross-sectional view of the safety sheath taken along the plane of line 13—13 in FIG. 12; and, FIG. 14 is a partial perspective view of the lower end of the syringe showing the knob on the barrel.

DETAILED DESCRIPTION OF THE PREFERRED EMBODIMENTS

Figure 1:
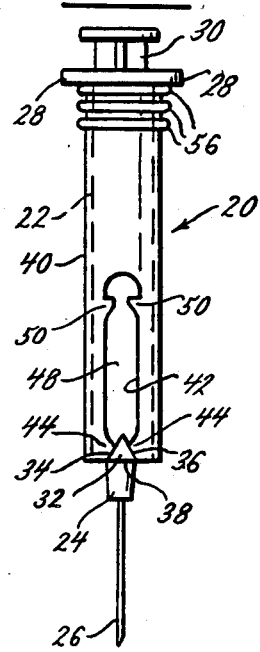
FIG. 1 is a side elevation view of a first embodiment of a syringe with a safety sheath constructed according to the principles of this invention, with the safety sheath in the retracted position.
Figure 2:
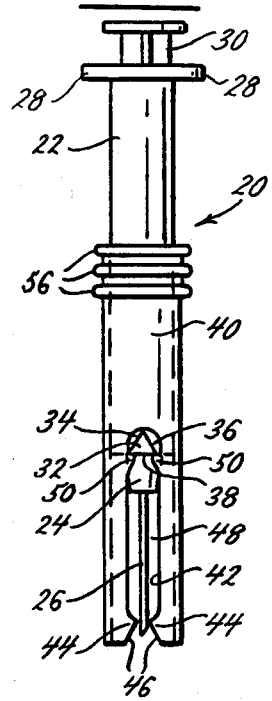
FIG. 2 is a side elevation view of the syringe with the safety sheath in the extended position.

A first embodiment of a syringe with a safety sheath constructed according to the principles of this invention is indicated generally as 20 in FIGS. 1 and 2. The syringe 20 comprises a barrel portion 22 terminating in a tip 24 at the lower end. Gradations or indicia (not shown) may be provided on the barrel 22 to indicate the volume in the syringe 20. A hypodermic needle 26 is mounted to the tip 24. Two diametrically opposed fingergrips 28 project radially outwardly from the top of the barrel 22. A plunger 30 reciprocates in the barrel 22 to draw and expel substances in the barrel 22.

Figure 3:
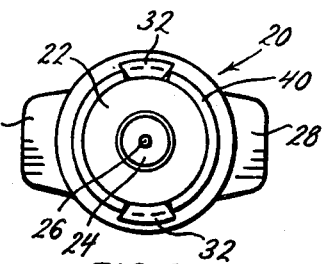
FIG. 3 is a bottom end view of the syringe as it is shown in FIG. 1.
Figure 4:
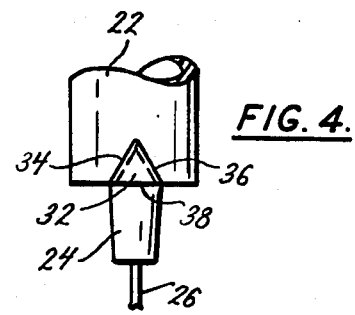
FIG. 4 is a partial side elevation view of the barrel of the syringe with the safety sheath removed, showing a knob.
Figure 6:
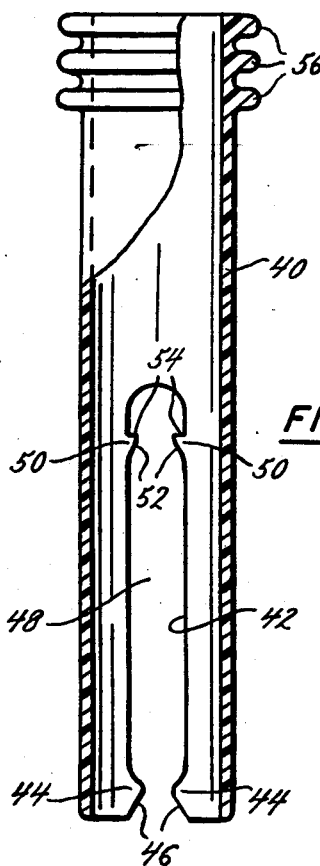
FIG. 6 is a side elevation view of the safety sheath with a portion broken away to show the interior.
Figure 5:
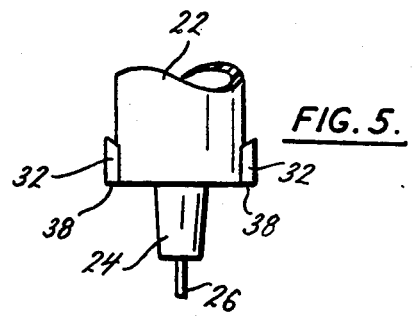
FIG. 5 is a partial side elevation view of the barrel of the syringe with the safety sheath removed, showing the knobs in profile.
Figure 7:
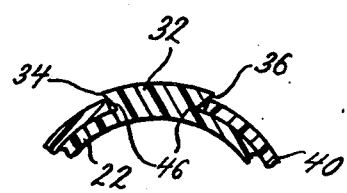
FIG. 7 is a partial cross-sectional view of the syringe taken along the plane of line 7—7 in FIG. 1, showing the engagement between the knob and the safety sheath.

At least one knob 32 projects radially outwardly near the bottom of the barrel 22. There are preferably two diametrically opposed knobs, as best shown in FIGS. 3 and 5. As shown in FIGS. 1-3, knobs 32 are preferably triangularly shaped with one of the vertices pointed upwardly. The upwardly facing left and right sides 34 and 36 of the knobs 32 are beveled to face radially inwardly, as best shown in FIGS. 3 and 7. The downwardly facing side 38 of the knob 32 extends generally horizontally, perpendicular to the axis of the syringe 20.

A sheath 40 is mounted on the barrel 22. The sheath 40 is preferably made of a resilient, transparent plastic so it does not mask the gradations or indicia on the barrel 22. The sheath 40 is slideable between a retracted position, shown in FIG. 1, and an extended position, shown in FIG. 2. The sheath 40 has a slot 42 to receive each knob 32 on the barrel 22. Thus, in the preferred embodiment there are two diametrically opposed slots 42 in the sheath 40 to accommodate the two knobs 32. The slots 42 extend upwardly from the bottom edge of the sheath 40. The slots 42 preferably extend through the thickness of the sheath 40. However, as discussed below, slot 42 could be replaced with a groove on the inside side of the sheath 40, in which case the sets of tabs hereinafter described might be replaced with some other means for engaging the knob 32.

A first pair of tabs 44 extend from opposite sides into each slot 42, near the lower end. The lower edges 46 of tabs 44 are angled downwardly and are also beveled to face radially outwardly. The central section 48 of slot 42 has generally parallel sides, and is sized to accommodate knob 32. A second pair of tabs 50 extend from opposite sides into slot 42, above the first pair of tabs 44 near the upper end of the slot 42. The lower edges 52 of the tabs 50 are angled downwardly, and the upper edges 54 of the tabs 50 extend generally horizontally to form shoulders perpendicular to the slot 42.

In the first preferred embodiment, a plurality of raised annular ribs 56 extend around the sheath 40 near the top to provide a grip to slide the sheath 40 relative to the barrel 22.

In FIG. 1, sheath 40 is in its retracted position. As shown in FIG. 7, the inwardly beveled sides 34 and 36 of the knobs 32 engage the outwardly beveled edges 46 of the tabs 44, to retain the sheath 40 against the barrel 22. The engagement between the lower edges 46 of the tabs 44 and the edges 34 and 36 of knob 32 helps to retain the sheath 40 in the retracted position. However, the angled edges 46 of the tabs 44 force the tabs 44 apart when sheath 40 is forced against the knob 32. The resiliency of the material that the sheath 40 is constructed from, and the presence of slots 42, permit the sheath 40 to flex sufficiently for the tabs 44 to clear the knob 32.

After tabs 44 clear the knob 32, the sheath 40 slides freely downwardly until the tabs 50 engage knob 32. The engagement between the tabs 50 and the knobs 32 resists further downward movement of the sheath 40. However, the angled lower edges 52 of the tabs 50 force the tabs 50 when sheath 40 is forced against the knob 32. Again, the resiliency of the material and the presence of slots 42 permit the sheath 40 to flex sufficiently for tabs 50 to clear the knob 32. After tabs 50 clear the knob 32, they resiliently snap back together, and the shoulders formed by upper edges 54 of the tabs 50 engage the bottom side 38 of the knob 32 to lock sheath 40 in its extended position. Thus locked, sheath 40 cannot move upward from its extended position, and sheath 40 blocks access to needle 26, preventing an accidental needlestick.

A second embodiment of a syringe with a safety sheath constructed according to the principles of this invention is indicated generally as 100 in FIGS. 8-10. Like syringe 20, syringe 100 comprises a barrel portion 102 terminating in a tip 104 at the lower end. Gradations or indicia (not shown) may be provided on the barrel 102 to indicate the volume in the syringe 100. A hypodermic needle 106 is mounted to the tip 104. Two diametrically opposed fingergrips 108 project radially outwardly from the top of the barrel 102. A plunger 110 reciprocates in the barrel 102 to draw and expel substances in barrel 102.

At least one knob 112 projects radially outwardly near the bottom of the barrel 102. As shown in FIGS. 11 and 14, in the preferred embodiment, knob 112 has an upwardly facing, upper face 114 that slopes radially outwardly in the downward direction. Knob 112 also has a downwardly facing, lower face 116, that is preferably perpendicular to the axis of the syringe 100.

A sheath 118, like sheath 40, is mounted on the barrel 102. The sheath 118 is preferably made of a resilient, transparent plastic so that it does not mask the gradations or indicia on the barrel 102. The sheath 118 is slideable between a retracted position, shown in FIGS. 8 and 9, and an extended position, shown in FIG. 10. The sheath 118 has a slot or groove 120 in its interior surface which, unlike the slot 42 in sheath 40, does not extend all the way through the wall of sheath 118. Thus, as best shown in FIGS. 8, 11, 12 and 13, groove 120 forms a tunnel 122 for receiving the knob 112 on the barrel 102.

As best shown in FIG. 11, first tab 124 extends from the bottom into the groove 120 near the lower end of the sheath 118. Tab 124 releasably engages the upper face 114 of the knob 112 when the sheath 118 is in its retracted position. This engagement helps to retain the sheath in its retracted position. The sloped face 114 of knob 112 forces the tab 124 outwardly when sheath 118 is forced downwardly. The resiliency of the material that sheath 118 is made from permits the sheath 118 to flex sufficiently for the tab 124 to clear the knob 112. Instead of tab 124, some other means for releasably engaging the knob 112 may be provided, for example a constriction in groove 120 or tabs extending from the sides of groove 120.

The central section 126 of groove 120 is sized to accommodate knob 112, and allow the sheath 118 to slide freely downwardly over knob 112.

A second tab 128 extends from the bottom into the groove 120, above tab 124 near the upper end of groove 120. As shown in the Figures, tab 128 can be formed by a constriction in tunnel 122. Tab 128 has a sloped lower face 130, and a flat upper face 132 generally perpendicular to the axis of the groove 120 to form a shoulder. The sloped lower face 130 of tab 128 releasably engages the upper face 114 of the knob 112. The sloped face 114 of knob 112 forces the tab 128 outwardly when sheath 118 is forced downwardly. Again, the resiliency of the material permits the sheath 118 to flex sufficiently for tab 128 to clear knob 112. After tab 128 clears the knob 112, it resiliently snaps back, and the shoulder formed by the upper face 132 of tab 128 engages the bottom face 116 of knob 112 to lock the sheath 118 in its extended position.

In the second preferred embodiment, a plurality of raised annular ribs 134 extend around the sheath 118 near the top to provide a grip to slide the sheath 118 relative to the barrel 102.

OPERATION

The syringe 20 of the first preferred embodiment may be provided with the sheath 40 in its retracted position as shown in FIG. 1. The syringe 20 may have a removeable cap (not shown) to help protect the needle 26 and keep it sterile. The cap is removed and syringe 20 can be used, for example to give an injection. After use, the contaminated needle 26 is not recapped. Instead, the sheath 40 is grasped by the raised ribs 56, and urged downwardly. The downward force applied to the sheath 40 urges the tabs 44 against the knob 32. The angled edges 46 of the tabs 44 force the tabs 44 apart to clear the knob 32. Once the tabs 44 clear the knob 32, the sheath 40 slides freely downwardly until the tabs 50 engage the knob 32. Continued downward pressure forces the tabs 50 against the knob 32. The angled lower edges 52 of the tabs 50 force the tabs 50 apart to clear knob 32. Once the tabs 50 clear the knob 32, the tabs snap resiliently back, locking the sheath 40 in its extended position. The shoulders formed by the top edges 54 of the tabs 50 engage the bottom side 38 of the knob 32, preventing the sheath 40 from moving upward.

The syringe 100 of the second preferred embodiment may be provided with the sheath 118 in its retracted position. The syringe 100 may have a removable cap (not shown) to help protect the needle 106 and keep it sterile. The cap is removed and syringe 100 can be used. After use, the contaminated needle 106 is not recapped. Instead, the sheath 118 is grasped and urged downwardly. The downward force applied to sheath 118 urges the tab 124 against the knob 112. The sloped upper face 114 of knob 112 forces tab 124 outwardly to clear knob 112. Once tab 124 clears the knob 112, the sheath 118 slides freely downwardly until the tab 128 engages knob 112. Continued downward pressure forces the tab 128 against knob 112. The sloped upper face 114 of the knob 112 forces tab 128 outwardly to clear knob 112. Once the tab 128 clears the knob 112, the tab snaps resiliently back, locking the sheath 118 in its extended position. The shoulder formed by the top face 132 of tab 128 engages the bottom face 116 of knob 112, preventing the sheath 118 from moving upwardly.

In either embodiment, in a simple, downward motion the needle is covered. The positive snap action and visual confirmation ensure that the sheath 40 is properly locked. The motion of bringing the needle and cap together is eliminated; the point of the needle is never directed toward the user and thus the potential for accidental needlestick is reduced.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. An improved syringe of the type comprising a barrel having a needle extending from the lower end, the improvement comprising:
   at least one knob extending outwardly from the barrel near the lower end;
   a sheath slideably mounted on the barrel and slideable between a retracted position over the barrel in which the sheath does not obstruct access to the needle and an extended position at least partly over the needle in which the sheath obstructs access to the needle;
   at least one longitudinal slot means in the sheath for receiving the knob, the slot means having means for releasably retaining the sheath in its retracted position, said releasable retaining means being releasable upon downward pressure applied to the sheath, the slot means further having means for lockingly engaging the knob to lockingly engage the sheath in the extended position.

2. The improved syringe of claim 1 wherein the slot means is an open slot extending through the wall of the sheath, for receiving the knob.

3. The improved syringe of claim 1 wherein the slot means is a longitudinal groove in the interior of the sheath for receiving the knob.

4. The improved syringe of claim 1 wherein the sheath has raised ribs at the upper end to aid in gripping the sheath.

5. The improved syringe of claim 1 wherein there are two knobs extending from the barrel at diametrically opposed locations, and wherein there are two slot means in the sheath, each slot means receiving one of the knobs.

6. The improved syringe of claim 2 wherein the knob is triangularly shaped, with one of the vertices oriented upwardly.

7. The improved syringe of claim 2 wherein the knob and the sheath have radially inwardly and outwardly beveled faces, respectively, that engage each other to retain the sheath against the barrel.

8. The improved syringe of claim 2 wherein the slot means extends upwardly from the lower end, the slot means having a first set of opposing tabs extending into the slot means near the lower end, the first set of tabs engaging the knob when the sheath is in the retracted position and releasably retaining the sheath in the retracted position, the first set of tabs having angled lower faces, these angled lower faces forcing the tabs apart to clear the knob when forced downwardly against the knob; the slot further having a second set of opposing tabs extending into the slot above the first set of tabs, near the upper end of the slot, the second set of tabs having angled lower faces and flat upper faces that form a shoulder, these angled lower faces forcing the tabs apart to clear the knob when forced against the knob, the second set of tabs resiliently snapping back after clearing the knob, the shoulders and the upper end of the slot cooperating to trap the knob and lock the sheath in the extended position.

9. The improved syringe of claim 8 wherein the lower faces of the first set of tabs are beveled to face radially outwardly and wherein the knob has faces beveled to face inwardly, the beveled faces on the knob engaging the beveled faces of the tab and retaining the sheath against the barrel.

10. An improved syringe of the type comprising a barrel having a needle extending from the lower end, the improvement comprising:
   at least one knob extending outwardly from the barrel near the lower end;
   a sheath slideably mounted on the barrel and slideable between a retracted position over the barrel in which the sheath does not obstruct access to the needle and an extended position at least partly over the needle in which the sheath obstructs access to the needle;
   at least one longitudinal slot in the sheath for receiving the knob, the slot having a first set of opposing tabs extending into the slot, the first set of tabs engaging the knob when the sheath is in the retracted position and releasably retaining the sheath in the retracted position, the first set of tabs having angled lower faces, these angled lower faces forcing the tabs apart to clear the knob when forced downwardly against the knob; the slot further having a second set of opposing tabs extending into the slot above the first set of tabs, the second set of tabs having angled lower faces and flat upper faces that form a shoulder, these angled lower faces forcing the tabs apart to clear the knob when forced against the knob, the second set of tabs resiliently snapping back after clearing the knob, the shoulders preventing upward movement of the sheath and locking the sheath in the extended position.

11. The improved syringe of claim 10 wherein the sheath has raised ribs at the upper end to aid in gripping the sheath.

12. The improved syringe of claim 10 wherein there are two knobs extending from the barrel at diametrically opposed locations, and wherein there are two slots in the sheath, each slot receiving one of the knobs.

13. The improved syringe of claim 10 wherein the knob is triangularly shaped, with one of the vertices oriented upwardly.

14. The improved syringe of claim 10 wherein the knob and the sheath have radially inwardly and outwardly beveled faces, respectively, that engage each other to retain the sheath against the barrel.

15. The improved syringe of claim 14 wherein the lower faces of the first set of tabs are beveled to face radially outwardly and wherein the knob has faces beveled to face inwardly, the beveled faces on the knob engaging the beveled faces of the tab and retaining the sheath against the barrel.

16. An improved syringe of the type comprising a barrel having a needle extending from the lower end, the improvement comprising:
   at least one knob extending outwardly from the barrel near the lower end, the knob having a generally triangular shape with one of the vertices oriented upwardly, and two of the faces of the triangle facing obliquely upwardly, the two upwardly facing faces being beveled to face generally radially inwardly;
   a sheath slideably mounted on the barrel and slideable between a retracted position over the barrel in which the sheath does not obstruct access to the needle and an extended position at least partly over the needle in which the sheath obstructs access to the needle;
   at least one longitudinal slot extending upwardly from the lower edge of the sheath for receiving the knob, the slot having a first set of opposing tabs extending into the slot, the first set of tabs engaging the knob when the sheath is in its retracted position and releasably retaining the sheath in its retracted position, the first set of tabs having angled lower faces, these angled lower faces forcing the tabs apart to clear the knob when forced downwardly against the knob, the lower faces of the first set of tabs further being beveled to face generally radially outwardly, the beveled faces on the knob engaging these beveled faces on the first set of tabs and retaining the sheath against the barrel; the slot further having a second set of opposing tabs extending into the slot above the first set of tabs, near the upper end of the slot, the second set of tabs having angled lower faces and flat upper faces that form a shoulder, these angled lower faces forcing the tabs apart to clear the knob when forced against the knob, the second set of tabs resiliently snapping back after clearing the knob, the shoulders and the end of the slot cooperating to trap the knob and lock the sheath in the extended position.

17. The improved syringe of claim 16 wherein the sheath has raised ribs at the upper end to aid in gripping the sheath.

18. The improved syringe of claim 16 wherein there are two knobs extending the barrel at diametrically opposed locations, and wherein there are two slots in the sheath, each slot receiving one of the knobs.

19. An improved syringe of the type comprising a barrel having a needle extending from the lower end, the improvement comprising:
    at least one knob extending outwardly from the barrel near the lower end;
    a sheath slideably mounted on the barrel and slideable between a retracted position over the barrel in which the sheath does not obstruct access to the needle and an extended position at least partly over the needle in which the sheath obstructs access to the needle;
    at least one longitudinal groove in the interior of the sheath for receiving the knob, the groove having first means for engaging the knob when the sheath is in the retracted position to retain the sheath in its retracted position; means for releasing the engagement between the first engaging means and the knob upon downward pressure applied to the sheath; and second means for engaging the knob when the sheath is in its extended position to lock the sheath in the extended position.

20. The improved syringe of claim 19 wherein the means for releasing the engagement between the first engaging means and the knob comprises a sloped surface on at least one of the tab or the first engaging means.

21. The improved syringe of claim 19 wherein the second means for engaging the knob comprises a means for defining a shoulder generally perpendicular to the groove and means on the knob for engaging the shoulder.

22. The improved syringe of claim 19 wherein the knob has a sloped upper face; and wherein the first engaging means comprises a tab extending from the bottom of the groove into the groove near the lower end.

* * * * *